United States Patent
Zhang et al.

(10) Patent No.: US 8,758,249 B2
(45) Date of Patent: Jun. 24, 2014

(54) METHOD AND APPARATUS FOR TISSUE DOPPLER IMAGING

(75) Inventors: Yu Zhang, Shenzhen (CN); Xin Li, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 2027 days.

(21) Appl. No.: 11/646,841

(22) Filed: Dec. 27, 2006

(65) Prior Publication Data

US 2008/0161691 A1    Jul. 3, 2008

(30) Foreign Application Priority Data

Oct. 23, 2006    (CN) .......................... 2006 1 0132042

(51) Int. Cl.
*A61B 8/00*    (2006.01)
(52) U.S. Cl.
USPC ........... 600/453; 600/437; 600/440; 600/441; 600/442; 600/449; 600/450; 600/454; 600/455
(58) Field of Classification Search
USPC ......... 600/437, 453, 440, 441, 442, 449, 450, 600/454, 455
See application file for complete search history.

(56) References Cited

U.S. PATENT DOCUMENTS

| | | | | |
|---|---|---|---|---|
| 5,482,044 A | * | 1/1996 | Lin et al. ........................ | 600/453 |
| 6,251,077 B1 | | 6/2001 | Mo et al. | |
| 6,776,759 B2 | * | 8/2004 | Heimdal et al. ............... | 600/442 |
| 8,206,302 B2 | * | 6/2012 | Zhang et al. ................... | 600/453 |
| 2007/0083118 A1 | * | 4/2007 | Dala-Krishna ................ | 600/437 |
| 2009/0018449 A1 | * | 1/2009 | Raju ............................. | 600/455 |

FOREIGN PATENT DOCUMENTS

| | | |
|---|---|---|
| CN | 1550217 | 12/2004 |
| JP | 2001037758 A | 2/2001 |

\* cited by examiner

*Primary Examiner* — Baisakhi Roy
(74) *Attorney, Agent, or Firm* — Kory D. Christensen; Stoel Rives LLP (57) ABSTRACT

A method for Tissue Doppler Imaging is provided. The method for Tissue, Doppler Imaging comprises steps of: a) transmitting ultrasound signals to a target area including the tissue to be imaged, and receiving the echo signals returned from the target area; b) performing Doppler estimation on Doppler signals extracted from the echo signals, to acquire Doppler parameters of stationary tissue or nonstationary tissue or blood flow within the target area, wherein the Doppler parameters comprise at least velocity and power; c) processing the acquired power of the Doppler parameters to obtain the power related to the nonstationary tissue within the target area, so as to display the tissue motion.

20 Claims, 6 Drawing Sheets
(3 of 6 Drawing Sheet(s) Filed in Color)

METHOD AND APPARATUS FOR TISSUE DOPPLER IMAGING

RELATED APPLICATION DATA

The application claims priority to Chinese Patent Application No. 200610132042.6, filed on Oct. 23, 2006, the entire disclosure of which is expressly incorporated by reference herein.

FIELD

The present application relates to a method and apparatus for ultrasound diagnostic imaging, more particularly to a method and apparatus for Tissue Doppler Imaging.

BACKGROUND

The Tissue Doppler Imaging (TDI) technique, which is developed based on the principle of Doppler frequency shift, is an ultrasound imaging technique for detecting and analyzing the motion and function of local tissue in vivo. Presently, the TDI technique is widely applied to the clinical diagnosis of cardiac muscle disease since it can make an accurate evaluation of the local tissue function, especially the function of cardiac muscles in a local area.

Figure 1:
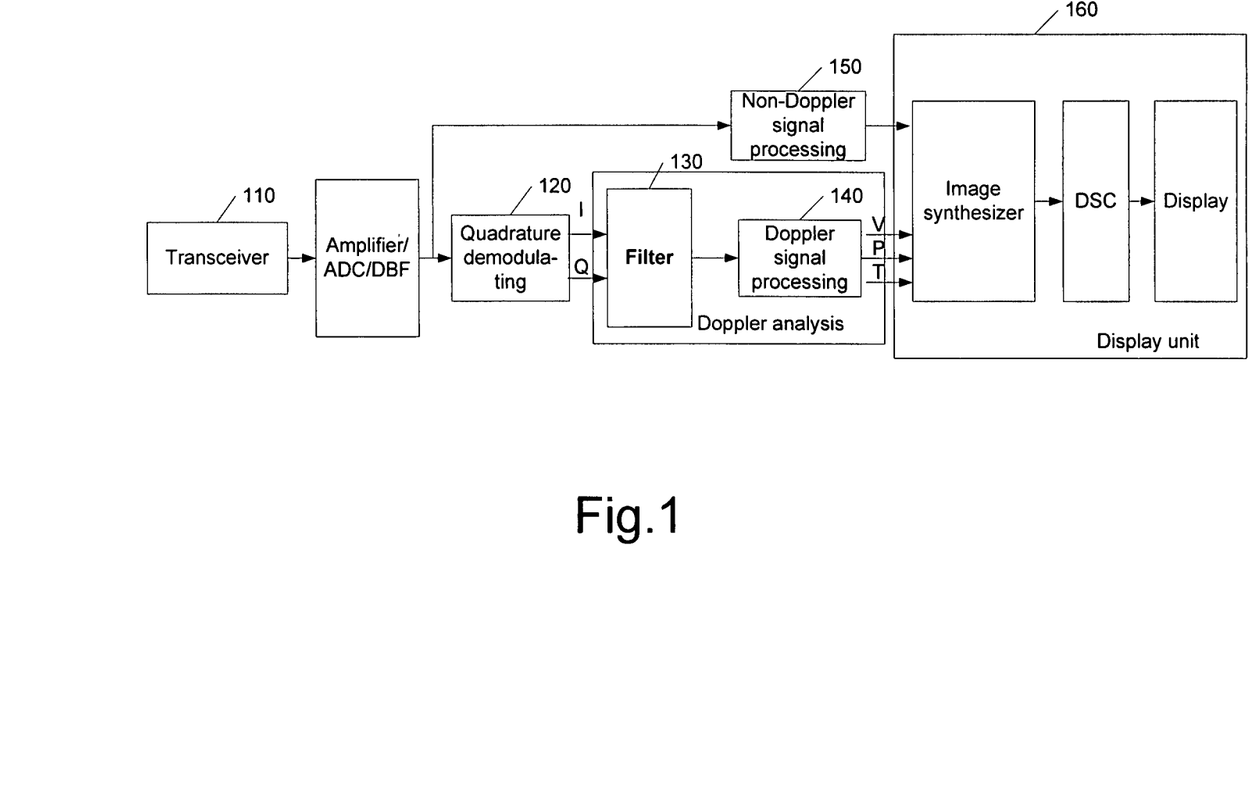
FIG. 1 is a diagram showing a conventional TDI system.

Both the cardiac blood flow and muscle show the different movement in a cardiac cycle. Currently, the color flow imaging technique has been able to present the motion of blood flow quite accurately. It has been noted that the motion of cardiac muscles is just different from that of blood flow in terms of the range of velocity and amplitude. Specifically, the blood flow signals are characteristic in having high-frequency and low-amplitude, while the signals for cardiac muscles are characteristic in having low-frequency and high-amplitude. Due to the difference between them, Tissue Doppler Imaging system may be obtained, on the basis of the conventional color flow Imaging technique, only by selecting the signals with low-frequency and high-amplitude, which corresponds to the cardiac muscle motion. This may be realized by modifying a filter and a gain controller in a practical color flow imaging system, FIG. 1 is a diagram for showing a TDI system in the prior art. As shown in FIG. 1, a transceiver unit 110 transmits ultrasound waves to a target area of interest in a human body such as the heart, and receives the echo signals returned from the targets. After being processed by a preamplifier, an analog digital converter (ADC) and a digital beam former (DBF), the received echo signals, in one path, are input into a unit 150 for non-Doppler signal processing, so as to directly display the anatomic configuration of the cardiac tissue in a display unit 160. In another path, the echo signals are input into a unit 120 for quadrature demodulating and then sent to the block of Doppler analysis. In the quadrature demodulating unit 120, the echo signals are quadrature demodulated into in-phase Doppler signal I and quadrature Doppler signal Q, which are then output to a filter 130 for obtaining the signals for cardiac muscle motion.

Subsequently, a Doppler signal processing unit 140 performs Doppler estimation on the signals output from the filter 130 in accordance with the similar manner as the Doppler flow imaging, for example, performing the autocorrelation estimation, Fast Fourier Transform (FFT), etc., so as to calculate motion parameters of the Doppler signals such as the frequency shift F, power P, variance T and so on. Wherein the frequency shift F of Doppler signals is proportional to the motion velocity V of a detected target based on the principle of Doppler effect, and thereby the velocity V is generally used to denote the frequency shift F, as shown in FIG. 1. The estimated motion parameters are then color encoded and input into a display unit 160. In the display unit 160, the encoded image of Doppler signals' motion parameters are mixed with the image of anatomic configuration for cardiac tissue, which is acquired by the non-Doppler signal processing, and at last the mixed image is presented on a screen after being converted by a Digital Scan Converter (DSC).

In the TDI system as shown in FIG. 1, in order to acquire accurate image for cardiac muscle motion, the design of the filter 130 is one of the critical steps, and also one of the challenging steps. With the rapid development of digital computer technology, researchers have proposed several methods to obtain the signals for cardiac muscle motion, for example, the method of applying a low-pass filter (LPF) to remove the blood flow signals, the method of bypassing the high-pass filter (HPF) in the conventional color flow imaging system to remove the blood flow signals, and the method of modifying the cutoff frequency of the original HPF, etc.

The main difference between the TDI systems designed according to the above methods is whether the HPF is applied. In the first method that the HPF is bypassed, the information regarding to the stationary tissue, blood flow and nonstationary cardiac muscle within a heart is all included in the extracted Doppler signals and is sent to unit 140 for Doppler estimation. Therefore, it is the image synthesizer to correctly distinguish the signals for cardiac muscle motion from other signals and display the obtained result. In this case, however, the image synthesizer can only remove blood flow signals having low-amplitude based on the signals' amplitude. For the echo signals from the stationary tissue that have relative high-amplitude, it is difficult to distinguish and remove them only based on the signals' amplitude. Consequently, by using this method, the noise caused by signals from the stationary tissue will be inevitably occurred in the images of cardiac muscle motion, thereby degrading the image quality.

The similar problem is also occurred in the second method of using a LPF to remove the blood flow information. In this method, despite the blood flow signals with high-frequency can be removed by a filter, the echo signals from the stationary tissue still exist together with the echo signals from the cardiac muscle, and they cannot be distinguished only based on the signals' amplitude. Thus, in the above two methods without a HPF, how to remove the echo signals from the stationary tissue is a problem to be resolved.

In the third method, the cutoff frequency of the HPF can be modified according to the velocity range of cardiac muscle motion (for example, being lowered appropriately), so that only the echo signals from the stationary tissue will be removed by the filter. It is obvious that the shortcomings of the above two schemes can be overcome in the third one. However, this modified HPF generally performs time domain filtering directly on the Doppler signals (I and Q) extracted from the echo signals, such as by using a Infinite Impulse Response (IIR) filter, and as a result this kind of filter needs large amounts of hardware resources when implemented in hardware, Moreover, the Tissue Doppler Imaging system is usually used for imaging the cardiac tissue motion, thus the imaging speed needs to be fast enough so as to track the status of the cardiac tissue motion. In other words, the imaging frame rate needs to be a relatively higher value. This requirement directly results in that the pulses repetition number on each scan line in one frame is decreased, which is generally 3 in a practical system. At the same time, the pulse repetition number determines the number of samples in quadrature Doppler signals that can be used for each range cell in each imaging operation. This means that, for each range cell, only a few (for example, 3) sampling points of the Doppler signals are sent to the filter and processed. However, when filtering the finite input signals, the inherent transient response of the filter will cause the frequency characteristics of input signals to be distorted. Especially as the filter order increases, which may be helpful to acquire perfect cutoff characteristics of the filter, the duration of the filter's transient response will be increased correspondingly, which results in a seriously adverse impact on the frequency characteristics of input signals.

Therefore, although the echo signals from the stationary tissue can be removed by modifying the cutoff frequency of the HPF, the filtering performed before the Doppler estimation will directly affect the accuracy of Doppler velocity estimation, thereby degrading the image quality of Doppler tissue velocity in a TDI system.

Based on the above analysis, it is difficult for TDI systems in the prior art to achieve satisfying image quality. Therefore, a new method and apparatus used for TDI is needed to address the above issues.

SUMMARY

An object is to provide a method and apparatus for Tissue Doppler Imaging, which is capable of achieving accurate Doppler velocity estimation by removing the signals from the stationary tissue and the blood flow.

Another object is to provide a method and apparatus for Tissue Doppler Imaging, which is capable of reducing hardware resource consumption of a filter and being implemented via hardware (e.g. FPGA) or software easily and effectively.

According to one aspect, a method for Tissue Doppler Imaging is provided. The method for Tissue Doppler Imaging comprises steps of: a) transmitting ultrasound signals to a target area including the tissue to be imaged, and receiving the echo signals returned from the target area; b) performing Doppler estimation on Doppler signals extracted from the echo signals, to acquire Doppler parameters of stationary tissue or nonstationary tissue or blood flow within the target area, wherein the Doppler parameters comprise at least velocity and power; c) processing the acquired power of the Doppler parameters to obtain the power related to the nonstationary tissue within the target area, so as to display the tissue motion.

According to another aspect, an apparatus for Tissue Doppler Imaging is provided. The an apparatus for Tissue Doppler Imaging comprises a transceiver unit for transmitting ultrasound signals to a target area including the tissue to be imaged, and receiving echo signals returned from the target area; a Doppler processing unit for performing Doppler estimation on Doppler signals extracted from the echo signals, to acquire Doppler parameters of stationary tissue or nonstationary tissue or blood flow within the target area, wherein the Doppler parameters comprise at least velocity and power; a filter for processing the power of the Doppler parameters to acquire the power related to the nonstationary tissue, so as to display the tissue motion.

The above method and apparatus may eliminate the degradation of estimation accuracy of the Doppler velocity caused by the filter calculating before the Doppler estimation, so as to improve the image quality. At the same time, by using the method and apparatus, the direct time domain IIR filtering for the Doppler signals extracted from the echo signals may be avoided, so as to save large numbers of hardware resources, and it is easy to implement the filter by a hardware or software promptly.

Other objects and attainments will become apparent and appreciated by referring to the following description and claims taken in conjunction with the accompanying drawings.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION

As described above, the echo signals from the moving tissue (e.g. the moving cardiac muscles) are characteristic in having low-frequency and high-amplitude. In other words, the echo signals from the cardiac muscles have a better Signal to Noise Ratio (SNR). Thus, the motion parameters with high accuracy may be acquired, even through fewer samples of the Doppler signals (e.g. 3 samples) are used to perform the Doppler estimation. Therefore, it is of advantage to perform the Doppler estimation directly on the Doppler signals before filtering, so as to acquire the accurate motion parameters such as the velocity V, power P, variance T and so on.

Moreover, in the Tissue Doppler Imaging, the quadrature Doppler signals acquired within each small range cell have very narrow bandwidth, and the velocity of tissue motion may be considered unchanged within the duration of smaller pulse repetition number (e.g. 3). Thus, the quadrature Doppler signals extracted from the echo signals can further be regarded as single-frequency signals with a fixed frequency. When a single-frequency signal is filtered, the signals before and after filtering will have the same frequency and bandwidth (namely, the variance acquired by Doppler estimation is unchanged), but the signal's amplitude after filtering will be attenuated according to the frequency response of the filter. Therefore, the filters in a TDI system can be considered as only affecting the amplitude of Doppler signals.

Based on the above two points, embodiments according to the present application are provided. In the TDI system according to one embodiment, the Doppler estimation is performed directly on the quadrature Doppler signals extracted from the echo signals, so as to calculate the motion parameters of the Doppler signals, such as the velocity V, power P, variance T and so on. Then, the acquired Doppler signals' power P is processed to acquire the one related to tissue motion (e.g. cardiac muscle motion). In this way, the acquired power P related to tissue motion and corresponding velocity V can perfectly describe the characteristics of tissue motion in the target area.

According to an embodiment, the TDI system shown in FIG. 1 is improved. In the improved TDI system according to an embodiment, all of the parts except for the improved Doppler analysis part are same as those in the TDI system of FIG. 1. Wherein, the improved Doppler analysis part starts from receiving the quadrature Doppler signals from the quadrature demodulating unit 120, and ends at outputting the motion parameters to the image synthesizer. Therefore, only the improved part will be described in detail below, and the detailed description about the other same units will be omitted.

Figure 2:
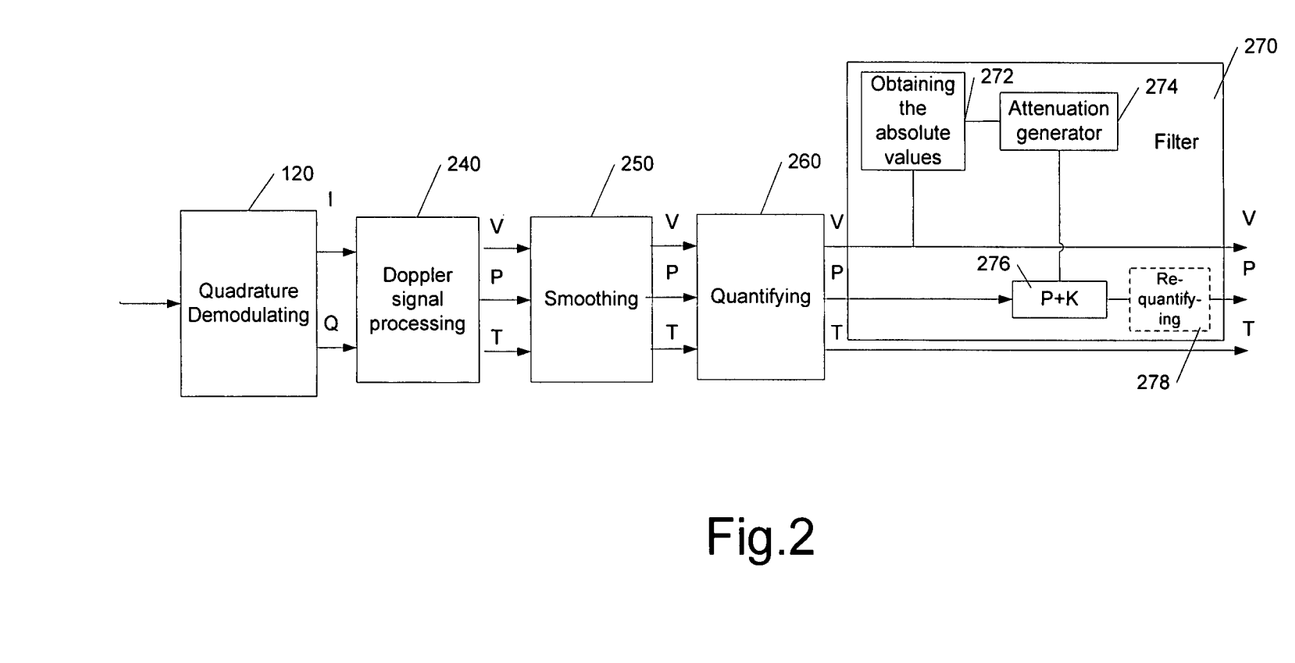
FIG. 2 is a block diagram for illustrating the configuration of the Doppler analysis part of the TDI system according to an embodiment.

FIG. 2 shows a block diagram of Doppler analysis part in the TDI system according to an embodiment. As shown in FIG. 2, the quadrature Doppler signals (I and Q) output from the quadrature demodulation unit 120 will not be filtered in time domain directly, as shown in FIG. 1 (for example, be processed by the filter 130). On the contrary, the quadrature Doppler signals (I and Q) are first input into a Doppler estimation unit 240 to perform the Doppler estimation, such as the autocorrelation estimation, to acquire the motion parameters of moving targets, such as the velocity V, power P, variance T and so on. Here, the motion parameters acquired directly according to the quadrature Doppler signals contain the information regarding to the motion of all targets within the target area. For example, when a detected target within the target area is the heart of a human body, the motion parameters estimated by the Doppler estimation unit 240 may comprise not only the parameters related to the cardiac muscle motion, but also those related to the stationary tissue and blood flow within the target area.

Next, the estimated motion parameters are smoothed in smoothing unit 250, in order to reduce the errors caused by noise. The smoothed parameters are then quantified and converted into digital values within a display range. For example, the parameters such as velocity, power, variance, and so on may be quantified and converted into digital values between 0-255, and then sent to the display unit 160 to be presented on a screen. Among the parameters, the power P may vary in a relatively large dynamic range. For this reason, the power P is logarithmically compressed, and then quantified into digital values between 0-255.

After being quantified, the motion parameters such as velocity V, power P and variance T are input into a filter 270 for selecting the power P related to the tissue motion (e.g. cardiac muscle motion). Actually, the filter 270 is designed according to the velocity range of the tissue motion, in order to remain the power P within a desired velocity range and remove those out of the desired range. For example, in the case of detecting cardiac muscle motion, the filter 270 is designed to remove or attenuate the power P in a velocity range of the stationary tissue motion (e.g. 0~1 cm/s) and/or the power P in a velocity range of the blood flow motion (e.g. greater than 15 cm/s). In this embodiment, the filter 270 may be a digital IIR or FIR filter, or may be an analog filter. The detailed procedure of how to obtain the filter 270 of this embodiment will be described below by taking a third-order Butterworth filter as an example.

Referring to FIG. 2, the cutoff frequency of the filter 270 will be first set according to the desired velocity range as shown above, and the order of the filter (e.g. third-order) is determined based on the desired cutoff characteristic. Then, the coefficients $a_i$ and $b_i$ of an IIR filter may be calculated from the determined cutoff frequency and the order. In this way, the designed IIR filter can be denoted as the following analytic equation:

$$H(z) = \frac{\sum_{i=0}^{p} b_i z^{-i}}{\sum_{i=0}^{q} a_i z^{-i}} \quad (1)$$

Then, substitute $z=\exp\{j2\pi f\}$ into equation (1) to get the frequency response function of the filter, which is shown as:

$$|H(f)| = \frac{\left|\sum_{i=0}^{p} b_i \exp\{j2\pi f i\}\right|}{\left|\sum_{i=0}^{q} a_i \exp\{j2\pi f i\}\right|} \quad (2)$$

Figure 3:
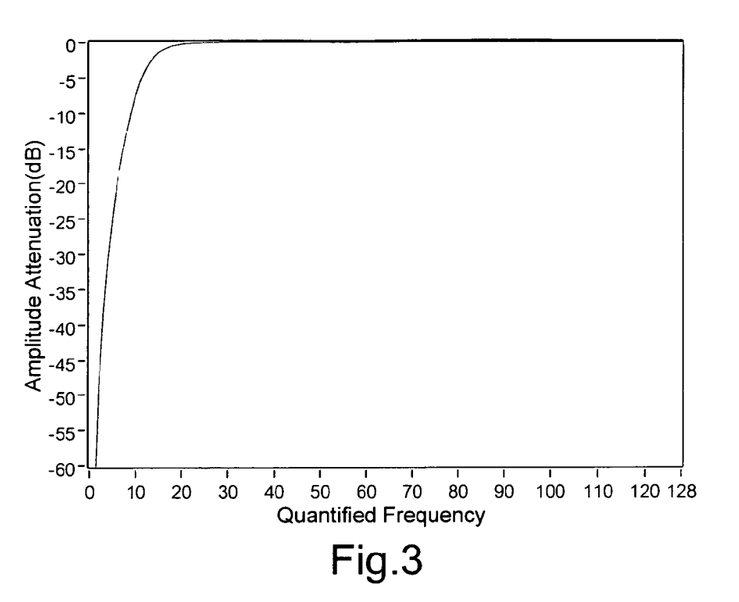
FIG. 3 is a diagram showing the frequency-amplitude characteristic of the filter designed according to an embodiment.

From the above equations, it can be seen that the amplitude-frequency response function of the filter can be acquired by performing FFT on the coefficients $a_i$ and $b_i$ respectively and then dividing the absolute value of FFT result for coefficients $b_i$ by that for $a_i$. The frequency response of the filter is symmetrical in positive and negative frequency range. If 256 points are used for performing FFT, the amplitude-frequency response of the filter will be similar to a HPF as shown in FIG. 3. In FIG. 3, the horizontal coordinate is quantified frequency ranging from 0 to 127, which corresponds to the digital angular frequency from 0 to π for the frequency shift of Doppler signals. The vertical coordinate is the amplitude attenuation coefficient K (here, the coefficient K is a logarithmic compressed value and shown in dB). As shown in FIG. 3, the filter 270 of the present embodiment is configured in such a way that the attenuation of the signals with about 0 frequency shift approximates to minus infinite, such as −200 dB herein, and thereby the filter 270 is capable of removing the echo signals from the stationary tissue.

After the filter 270 is well designed, the frequency response function of the filter 270, i.e. the equation (2) will be stored in a memory. Alternatively, the relationship between velocity (frequency shift) and amplitude attenuation coefficient K will be stored as a lookup table of velocity versus amplitude attenuation. Then, an absolute value of the velocity V is obtained in a unit 272 of the filter 270, so as to eliminate the direction of the velocity. The obtained velocity is further quantified and converted into a digital value in a range of 0 to 127. Later, an attenuation generator 274 in the filter 270 searches in the stored lookup table to find the amplitude attenuation coefficient K that corresponds to the quantified velocity V output of the unit 272. In the present embodiment, the same logarithmic compression and quantification are performed on both the amplitude attenuation coefficient K and the power P. Thus, in an attenuator 276, the operation of attenuating the power P, or called filtering, may be implemented by adding the quantified power P with the amplitude attenuation coefficient K generated by the attenuation generator 274. In order to acquire better Doppler power image for the tissue motion, a re-quantifying unit may be added next to the attenuator 276, so as to re-adjust the added result to the display range of 0 to 255.

After filtering, the parameters, which includes the power P processed by the filter 270, the corresponding velocity V and variance T, are all sent to an image synthesizer of the display unit 160 to be synthesized with the image of tissue anatomic configuration acquired by the non-Doppler processing. In the present embodiment, the filter 270 only removes the power P of the signals from stationary or near-stationary tissue, so the image synthesizer must still remove the blood flow signals, which have low-amplitude, by a threshold decision on signals' amplitude. At last, the image of tissue motion (cardiac muscle motion) with good quality and high accuracy will be displayed on a screen.

One embodiment is described in accordance with FIG. 2 as above. It is to be understood by those skilled in the art that various improvements and modifications may be made to each part of the embodiment.

For example, when the filter 270 is implemented, the step of obtaining the absolute value of velocity V may not be necessary. In this case, the frequency response function of the filter is stored directly as a lookup table, which contains the positive and negative frequency shift (or velocity), such that the velocity may be used directly for looking up the table.

Moreover, when the frequency response function of the filter may be denoted by an analytic equation, the attenuation generator may also acquire the amplitude attenuation coefficient K in real-time by substituting the current velocity into the analytic equation and obtaining the solution to the analytic equation directly.

Furthermore, in above embodiment, the filter 270 is designed as a HPF (as shown in FIG. 3). In practical application, however, the filter 270 may be designed as a band-pass filter, so as to remove the signals from the stationary tissue and the blood flow signals at the same time.

In addition, in an alternative embodiment, the logarithmic compression may not be performed directly on the power P and the amplitude attenuation. In this case, the square of power P is first multiplied with the square of the amplitude attenuation coefficient K to implement the attenuation, and then the logarithmic compression is performed on the product of power P and coefficient K in the re-quantification unit.

Figure 4:
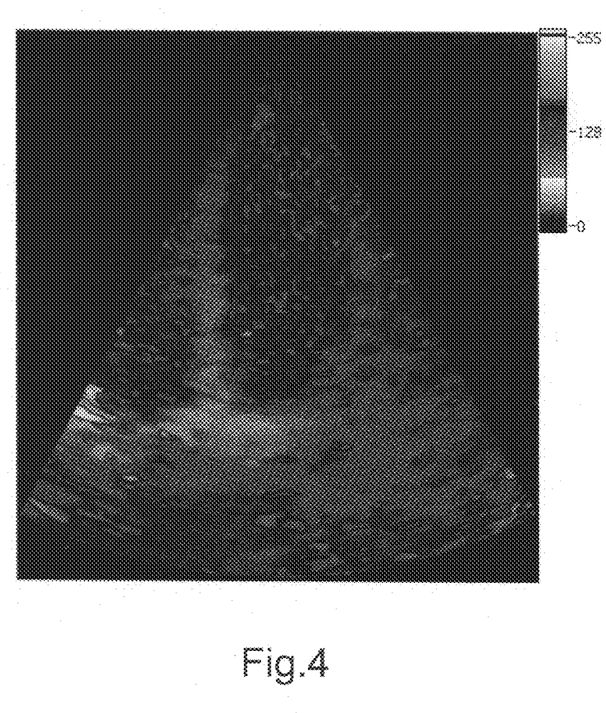
FIG. 4 shows a Doppler velocity image acquired by using the TDI system according to an embodiment.

Hereinbefore, the TDI system and the method thereof are described in detail in connection with the embodiments. FIG. 4 shows a TDI velocity image of echo signals from a heart, which is obtained by using the TDI system. As shown in FIG. 4, since the Doppler estimation is directly performed on the Doppler signals before filtering, even under the circumstances that there is only few number of sampling points, a relative high accuracy of Doppler velocity may still be achieved by the Doppler estimation.

Figure 5:
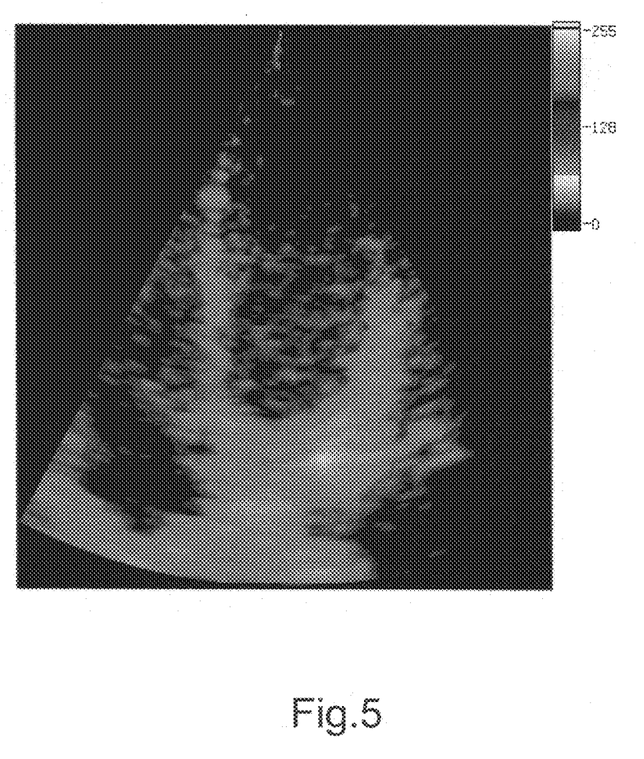
FIG. 5 shows a Doppler power image obtained in a conventional TDI system.
Figure 6:
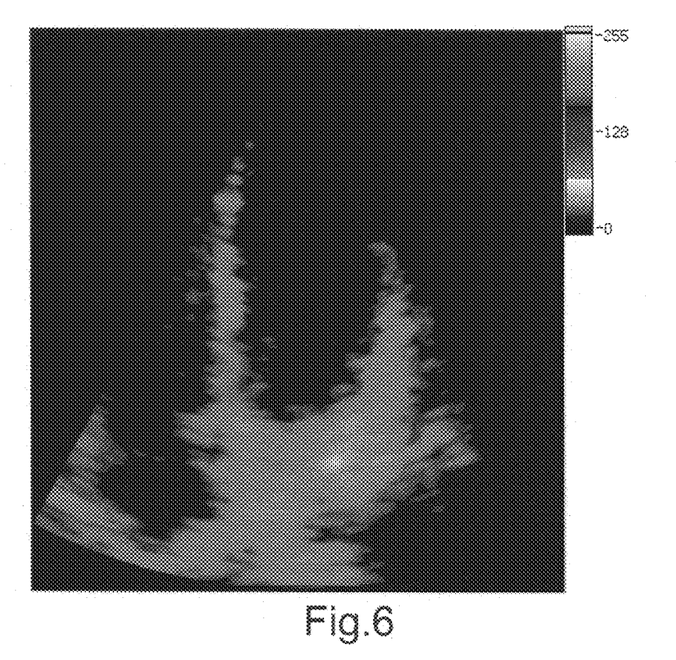
FIG. 6 shows a Doppler power image acquired by using the TDI system according to an embodiment.

FIG. 5 shows a TDI power image without filtering. As shown in FIG. 5, more tissue power remains at the locations close to the skin surface and within the chambers of heart, however, these parts of tissue are generally stationary and undesired. FIG. 6 shows a TDI power image acquired by using the TDI system according to an embodiment. As shown in FIG. 6, the interference signals from the stationary tissue in FIG. 5 are mostly removed, so that the image quality is improved.

Moreover, the Doppler signals' power P is processed in frequency domain, consequently, the complex filtering in time domain is transformed into simple amplitude attenuation in frequency domain. In addition, the processing in frequency domain substantially can be implemented by simply looking up table and adding operation, so that a large amount of hardware resources are saved, and the calculating efficiency is improved.

It is to be understood by those skilled in the art that various improvements and modifications may be made to the apparatus and method for Tissue Doppler Imaging as disclosed without departing from the basis of the present invention, the scope of which is to be defined by the appended claims herein.

What is claimed is:

1. A method for Tissue Doppler Imaging, comprising the steps of:

a) transmitting ultrasound signals to a target area including the tissue to be imaged, and receiving the echo signals returned from the target area;
b) before filtering Doppler signals extracted from the echo signals, performing Doppler estimation directly on the Doppler signals extracted from the echo signals, to acquire Doppler parameters of stationary tissue and nonstationary tissue or blood flow within the target area, wherein the Doppler parameters comprise at least velocity and power; and
c) filtering, based on the acquired velocity of the Doppler parameters of stationary tissue and nonstationary tissue or blood flow, the acquired power of the Doppler parameters of stationary tissue and nonstationary tissue or blood flow to obtain the power related to the nonstationary tissue within the target area, so as to display the tissue motion.

2. The method of claim 1, wherein the filtering step comprises:
pre-designing a filter according to a predetermined velocity range of the tissue motion, so as to process the power.

3. The method of claim 2, wherein the filtering step further comprises:
attenuating the power in frequency domain based on a frequency response of the filter.

4. The method of claim 3, wherein the attenuating step comprises:
acquiring a relationship between attenuation and velocity based on an amplitude-frequency response of the filter; and
acquiring the attenuation for the power from the corresponding velocity of the Doppler parameters, according to the acquired relationship.

5. The method of claim 4, wherein the attenuation is acquired by searching a look-up table.

6. The method of claim 4, wherein the attenuation is acquired by obtaining a solution to an analytic equation of the amplitude-frequency response.

7. The method of claim 4, wherein the attenuating step further comprises:
performing logarithmic compression on the power of the Doppler parameters to obtain a logarithmic value of the power; and
performing logarithmic compression on the attenuation to obtain a logarithmic value of the attenuation.

8. The method of claim 7, wherein the attenuating step comprises:
adding the logarithmic value of the attenuation with the logarithmic value of the power.

9. The method of claim 1, wherein the tissue motion is cardiac muscle motion.

10. The method of claim 9, wherein the filtering step is to remove the Doppler signals for blood flow and/or stationary tissue within the target area.

11. An apparatus for tissue Doppler imaging, comprising:
a transceiver unit for transmitting ultrasound signals to a target area including the tissue to be imaged, and receiving echo signals returned from the target area;
a Doppler processing unit for performing, before filtering Doppler signals extracted from the echo signals, Doppler estimation directly on the Doppler signals extracted from the echo signals, to acquire Doppler parameters of stationary tissue and nonstationary tissue or blood flow within the target area, wherein the Doppler parameters comprise at least velocity and power; and
a filter for processing, based on the acquired velocity of the Doppler parameters of stationary tissue and nonstationary tissue or blood flow, the power of the Doppler parameters of stationary tissue and nonstationary tissue or blood flow to acquire the power related to the nonstationary tissue, so as to display the tissue motion.

12. The apparatus of claim 11, wherein the filter is designed according to a predetermined velocity range of the tissue motion.

13. The apparatus of claim 12, wherein the filter comprises:
an attenuation generator for generating attenuation for the power in frequency domain, based on frequency response of the filter; and
an attenuator for attenuating the power based on the generated attenuation.

14. The apparatus of claim 13, wherein the attenuation generator is configured to acquire a relationship between attenuation and velocity based on an amplitude-frequency response of the filter; and to generate the attenuation for the power from the corresponding velocity of the Doppler parameters, according to the acquired relationship.

15. The apparatus of claim 14, wherein the attenuation generator is configured to generate the attenuation by searching a look-up table.

16. The apparatus of claim 14, wherein the attenuation generator is configured to generate the attenuation by obtaining a solution to an analytic equation of the amplitude-frequency response.

17. The apparatus of claim 14, wherein the Doppler processing unit further performs logarithmic compression on the power to obtain a logarithmic value of the power; and the attenuation generator further performs logarithmic compression on the attenuation to obtain a logarithmic value of the attenuation.

18. The apparatus of claim 17, wherein the attenuator is an adder for adding the logarithmic value of the power with the logarithmic value of the attenuation.

19. The apparatus of claim 11, wherein the tissue motion is cardiac muscle motion.

20. The apparatus of claim 19, wherein the filter is configured to remove the Doppler signals for blood flow and/or stationary tissue within the target area.

* * * * *